US006750026B2

(12) United States Patent
Bergsma et al.

(10) Patent No.: US 6,750,026 B2
(45) Date of Patent: Jun. 15, 2004

(54) SCREENING METHODS USING LIGANDS OF THE NEUTROPEPTIDE RECEPTOR HFGAN72

(75) Inventors: Derk J. Bergsma, Berwyn, PA (US); David P. Brooks, West Chester, PA (US); Miklos Gellai, Devon, PA (US); Shelagh Wilson, Beckets Bramfield (GB); Masashi Yanagisawa, Dallas, TX (US)

(73) Assignees: SmithKline Beecham Corporation, Philadelphia, PA (US); Board of Regents The University of Texas System, Dallas, TX (US)

( * ) Notice: Subject to any disclaimer, the term of this patent is extended or adjusted under 35 U.S.C. 154(b) by 138 days.

(21) Appl. No.: 09/737,379

(22) Filed: Dec. 15, 2000

(65) Prior Publication Data

US 2002/0082202 A1 Jun. 27, 2002

Related U.S. Application Data

(60) Division of application No. 08/939,093, filed on Sep. 26, 1997, now Pat. No. 6,309,854, which is a continuation-in-part of application No. 08/887,382, filed on Jul. 2, 1997, now abandoned, which is a continuation-in-part of application No. 08/820,519, filed on Mar. 19, 1997, now abandoned.
(60) Provisional application No. 60/033,604, filed on Dec. 17, 1996.

(51) Int. Cl.$^7$ .......................... G01N 33/53; C12N 1/00; C12N 5/00; C07K 14/00

(52) U.S. Cl. ...................... 435/7.1; 435/4; 435/252.3; 435/325; 530/300; 530/324; 530/399

(58) Field of Search ................................. 530/300, 350, 530/324, 399; 435/4, 7.1, 325, 252.3

(56) References Cited

U.S. PATENT DOCUMENTS 6,001,963 A * 12/1999 Bergsma et al. ............ 530/324

FOREIGN PATENT DOCUMENTS

WO    WO 98/05352    2/1998

OTHER PUBLICATIONS

Sakurai et al. Orexins and orexin receptors: a family of hypothalamic neuropeptides and G protein–coupled receptors that regulate feeding behavior. Cell 92: 573–585, 1998.*
Smart et al. Characterization of recombinant human orexin receptor pharmacology in a Chinese hamster ovary cell–line using FLIPR. Br J Pharmacol. 128(1):1–3, 1999.*
Smart et al. SB–334867–A: the first selective orexin–1 receptor antagonist. Br J Pharmacol. 132(6):1179–1182, 2001.*

Risold, et al., "Preprohypocretin (Orexin) and Prolactin–Like Immunoreactivity are Coexpressed by Neurons of the Rat Lateral Hypothalamic Area," *Neuroscience Letters*, 259: pp. 153–156 (1999).

Schachter, et al., "Prolactin mRNA Exists in Rat Hypothalamus," *Endocrinology*, 114(5): pp. 1947–1949 (1984).

Valatx, et al., "Mise en Evidence d'ARN Messagers de la Prolactine Apres Amplification Dans Le Cerveau Du Rat," *C.R. Acad. Sci. Paris*, 315(3): pp. 295–301 (1992).

Emanuele, et al., "The Rat Prolactin Gene is Expressed in Brain Tissue: Detection of Normal and Alternatively Spliced Prolactin Messenger RNA," *Molecular Endocrinology*, 6: pp. 35–42 (1992).

Dutt, et al., "Prolactin, Central Nervous System and Behavior: A Critical Review," *Neuroendocrinology*, 59: pp. 413–419 (1994).

De Lecea, et al., "The Hypocretins: Hypothalamus–Specific Peptides With Neuroexcitatory Activity," *Proc. Natl. Acad. Sci. USA*, 95: pp. 322–327 (1998).

Grillon, et al., "Alteration of Dynorphin and Secretogranin II in the Prolactin Immunoreactive Neurons of the Rat Lateral Hypothalamus Upon Osmotic Stimulation," *Neuroscience Letters*, 208: pp. 33–36 (1996).

Fuxe, et al., "Prolactin–Like Immunoreactivity: Localization in Nerve Terminals of Rat Hypothalamus," *Science*, 196: pp. 899–900 (1977).

Peyron, et al., "Neurons Containing Hypocretin (Orexin) Project to Multiple Neuronal Systems," *The Journal of Neuroscience*, 18(23): 9996–10015 (1998).

Alonso, et al., "Axons Containing a Prolactin–Like Peptide Project into the Perivascular Layer of the Median Eminence: An Immunocytochemical Light and Electron Microscope Study in Adult and Infant Rats," *Neuroendocrinology*, 48: pp. 39–44 (1988).

Clapp, et al., "The Prolactin Gene is Expressed in the Hypothalamic–Neurohypophyseal System and the Protein is Processed into a 14–kDa Fragment with Activity Like 16–kDa Prolactin," *Proc. Natl. Acad. Sci. USA*, 91: pp. 10384–10388 (1994).

(List continued on next page.)

*Primary Examiner*—Elizabeth Kemmerer
*Assistant Examiner*—Bridget E. Bunner
(74) *Attorney, Agent, or Firm*—Andrea V. Lockenour; Elizabeth J. Hecht; Charles M. Kinzig

(57) ABSTRACT

Polypeptides of HFGAN72 receptor ligands and polynucleotides encoding the polypeptides are provided. Methods of using these polypeptides to diagnose diseases relating to the under- or over-expression of HFGAN72 receptor ligands are also provided. In addition, methods of identifying agonists or antagonists of the interaction of HFGAN72 receptor ligands with the HFGAN72 receptor are provided. Methods of treatment by administering the identified agonists or antagonists to patients in need thereof are further disclosed.

2 Claims, 5 Drawing Sheets

OTHER PUBLICATIONS

Griffond, et al., "Occurrence of Secretogranin II in the Prolactin–Immunoreactive Neurons of the Rat Lateral Hypothalamus: An In Situ Hybridization and Immunocytochemical Study," *Journal of Chemical Neuroanatomy*, 9: pp. 113–119 (1995).

Paut–Pagano, et al., "Anatomical Distribution of Prolactin–Like Immunoreactivity in the Rat Brain," *Neuroendocrinology*, 58: pp. 682–695 (1993).

Bahjaoui–Bouhaddi, et al., "Induction of Fos–Immunoreactivity in Prolactin–Like Containing Neurons of the Rat Lateral Hypothalamus After Insulin Treatment," *Neuroscience Letters*, 168: 11–15 (1994).

Griffond, et al., "Evidence for the Expression of Dynorphin Gene in the Prolactin–Immunoreactive Neurons of the Rat Lateral Hypothalamus," *Neuroscience Letters*, 165: pp. 89–92 (1994).

* cited by examiner

Figure 1

```
aaaacataatgtgggtctcgcgtctgcctctctcccgcccctaattagcagctgcctccc
tccatattgtcccaggccagcgcttcttttgtgctcccagattcctgggtgcaaggtggc
ctcattagtgcccggagaccgcccatctccagggagcagatagacagacaaggggggtga
tcaggggcacagtgatccaaccctggcctctgaacgccgcagcggccattccttgggccc
agcctggagacggccccctgcagcaggctaatcttagacttgcctttgtctggcctggg
tgtggacgcaatgtgcctgtcaattccccgccacctcagagcactataaacccagaccc
ctgggagtgggtCACAATTGACAGCCTCAAGGTTCCTGGCTTTTTGAACCACCACAGACA
TCTCCTTTCCCGGCTACCCCACCCTGAGCGCCAGACACCATGAACCTTCCTTCCACAAAG
gtaaagatccagggatggaggggtgactcagccatcccagaggaagcaaaaagagtgctt
gctcagagggctggaagaaaggccaaaggtgtctccactcttggtcttttcctgggtgtg
ctctgaggcaggagcacctgccttggctcacattgggttgggtgctgttttgctaagagc
ctgtgtttgctgagctcatatgtgtcaggtgctccgtttgcacctgtcatctcttgtcat
cctcccaacagccttgcagagtagaaattatttctagtatacccagtttacaggtaaggg
agctgtgccctctgaaagggcaggaaactggttcaaagcaacggagttcagtcactcctg
caagggggcaggcagatgagagagcattctggagtcttgctagttcctgatttccatgtg
tttccctgctgtggagaggaagttggggggactcagtagggcccgggttttttcccaagtt
tacaacttctgctgcagacagacactcctgttttcaggtggagtggcaagtgccctagtg
gtggcaacagtggcctaagtctccagagaaaagggggattcactctgcccaggggggtctc
aaaaggcttcctgtgggagatgctctgctgggtcttgaaggaggagcagggaaagtaggc
cgataccagcaagggcgcaaagcaaggagaactaagtgacagccagaaaggagtgcaggc
ttggagggggcgcggagccagaggggcaggtcctgtgcgtgggagctggtggcgggcgcc
gtgggaagacccccccagcgccctgtctccgtctccctag
GTCTCCTGGGCCGCCGTGACGCTACTGCTGCTGCTGCTGCTGCCGCCCGCGCTGTTG
TCGTCCGGGCGGCTGCACAGCCCCTGCCCGACTGCTGTCGTCAAAAGACTTGCTCTTGC
CGCCTCTACGAGCTGCTGCACGGCGCGGGCAATCACGCGGCCGGCATCCTCACGCTGGGC
AAGCGGAGGTCCGGGCCCCCGGGCCTCCAGGGTCGGCTGCAGCGCCTCCTGCAGGCCAGC
GGCAACCACGCCGCGGGCATCCTGACCATGGGCCGCCGCGCAGGCGCAGAGCCAGCGCCG
CGCCCCTGCCTCGGGCGCCGCTGTTCCGCCCCGGCCGCCGCCTCCGTCGCGCCCGGAGGA
CAGTCCGGGATCTGAGTCGTTCTTCGGGCCCTGTCCTGGCCCAGGCCTCTGCCCTCTGCC
CACCCAGCGTCAGCCCCCAGAAAAAAGGCAATAAAGACGAGTCTCCATTcgtgtgactgg
tctctgttcctgtgcggtcgcgtcctgcccatccggggtggcaaagcgtcttgcggagga
cagctgggcctggaagcccggctgtcgggcaccagccttagcttttgcgtggttgaatcg
gaaacactcttggttggggagttcccagtgcaaggccctggggcacagagagaactgcac
aggtgcatgc
```

Figure 2

```
M    N    L    P    S    T    K
V    S    W    A    A    V    T    L    L    L    L    L    L    L    L    P    P    A    L    L
S    S    G    A    A    A    Q--P--L--P--D--C--C--R--Q--K--T--C--S--C-
R--L--Y--E--L--L--H--G--A--G--N--H--A--A--G--I--L--T--L    G
K    R    RSGPPGLQGRLQRLLQA**S*
GNHAAGILT**M    G    R    R    A    G    A    E    P    A    P
R    P    C    L    G    R    R    C    S    A    P    A    A    A    S    V    A    P    G    G
Q    S    G    I
```

Figure 3

```
  1  GGC TCG GCG GCC TCA GAC TCC TTG GGT ATT TGG ACC ACT GCA CCG
 46  AAG ATA CCA TCT CTC CGG ATT GCC TCT CCC TGA GCT CCA GAC ACC
191  ATG AAC CTT CCT TCT ACA AAG GTT CCC TGG GCC GCC GTG ACG CTG
136  CTG CTG CTG CTA CTG CTG CCG CCG GCG CTG CTG TCG CTT GGG GTG
181  GAC GCG CAG CCT CTG CCC GAC TGC TGT CGC CAG AAG ACG TGT TCC
226  TGC CGT CTC TAC GAA CTG TTG CAC GGA GCT GGC AAC CAC GCC GCG
271  GGC ATC CTC ACT CTG GGA AAG CGG CGA CCT GGA CCC CCA GGC CTC
316  CAA GGA CGG CTG CAG CGC CTC CTT CAG GCC AAC GGT AAC CAC GCA
361  GCT GGC ATC CTG ACC ATG GGC CGC CGC GCA GGC GCA GAG CTA GAG
406  CCA TAT CCC TGC CCT GGT CGC CGC TGT CCG ACT GCA ACC GCC ACC
451  GCT TTA GCG CCC CGG GGC GGA TCC AGA GTC TGA ACC CGT CTT CTA
496  TCC CTG TCC TAG TCC TAA CTT TCC CCT CTC CTC GCC GGT CCC TAG
541  GCA ATA AAG ACG TTT CTC TGC TAA AAA AAA AAA AAA AAA AAA AAA
```

```
V  P  W  A  A  V  T  L  L  L  L  L  L  P  P  A  L  L  S  L  G
V  D  A  Q--P--L--P--D--C--C--R--Q--K--T--C--S--C--R--L--Y--E--L-
L--H--G--A--G--N--H--A--A--G--I--L--T--L  G  K  R  RPGPP*
GLQGRLQRLLQANGNHAAGILTM
G  R  R  A  G  A  E  L  E  P  H  P  C  S  G  R  G  C  P  T  V  T  T
T  A  L  A  P  R  G  G  S  G  V
```

SCREENING METHODS USING LIGANDS OF THE NEUTROPEPTIDE RECEPTOR HFGAN72

CROSS-REFERENCE TO RELATED APPLICATIONS

This application is a divisional of U.S. application Ser. No.: 08/939,093, filed Sep. 26, 1997, now U.S. Pat. No. 6,309,854, granted on Oct. 30, 2001, which is a continuation-in-part application of U.S. application Ser. No. 08/887,382, which was filed on Jul. 2, 1997, now abandoned, which is a continuation-in-part application of U.S. application Ser. No. 08/820,519, which was filed on Mar. 19, 1997, now abandoned, which claims priority to the earlier provisional U.S. application, Ser. No. 60/033,604, which was filed on Dec. 17, 1996, the contents of which are herein incorporated by reference in their entirety.

FIELD OF THE INVENTION

This invention relates to newly identified polypeptides and polynucleotides encoding the polypeptides; variants and derivatives of the polypeptides and polynucleotides; agonists and antagonists of the polypeptides; and uses of the polypeptides, polynucleotides, variants, derivatives, agonists and antagonists. In particular, in these and in other regards, the invention relates to polypeptides and polynucleotides encoding polypeptides which are ligands for the neuropeptide receptor HFGAN72, hereinafter referred to as "HFGAN72 receptor ligands".

BACKGROUND OF THE INVENTION

This invention relates to newly identified polynucleotides, polypeptides encoded by such polynucleotides, the use of such polynucleotides and polypeptides, as well as the production of such polynucleotides and polypeptides. More particularly, the polypeptides of the present invention are ligands for a human 7-transmembrane receptor. The invention also relates to inhibiting or activating the action of such polypeptides.

It is well established that many medically significant biological processes are mediated by proteins participating in signal transduction pathways that involve G-proteins and/or second messengers, e.g., cAMP (Lefkowitz, *Nature*, 1991, 351:353–354). Herein, these proteins are referred to as proteins participating in pathways with G-proteins or PPG proteins. Some examples of these proteins include the GPC receptors, such as those for adrenergic agents and dopamine (Kobilka, B. K., et al., *Proc. Natl Acad Sci., USA*, 1987, 84:46–50; Kobilka, B. K., et al., *Science*, 1987, 238:650–656; Bunzow, J. R., et al., *Nature*, 1988, 336:783–787), G-proteins themselves, effector proteins, e.g., phospholipase C, adenyl cyclase, and phosphodiesterase, and actuator proteins, e.g., protein kinase A and protein kinase C (Simon, M. I., et al., *Science*, 1991, 252:802–8).

For example, in one form of signal transduction, the effect of hormone binding is activation of the enzyme, adenylate cyclase, inside the cell. Enzyme activation by hormones is dependent on the presence of the nucleotide GTP. GTP also influences hormone binding. A G-protein connects the hormone receptor to adenylate cyclase. G-protein was shown to exchange GTP for bound GDP when activated by a hormone receptor. The GTP-carrying form then binds to activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane α-helices connected by extracellular or cytoplasmic loops. G-protein coupled receptors include a wide range of biologically active receptors, such as hormone, viral, growth factor and neuro-receptors.

G-protein coupled receptors have been characterized as including these seven conserved hydrophobic stretches of about 20 to 30 amino acids, connecting at least eight divergent hydrophilic loops. The G-protein family of coupled receptors includes dopamine receptors, which bind to neuroleptic drugs used for treating psychotic and neurological disorders. Other examples of members of this family include, but are not limited to, calcitonin, adrenergic, endothelin, cAMP, adenosine, muscarinic, acetylcholine, serotonin, histamine, thrombin, kinin, follicle stimulating hormone, opsins, endothelial differentiation gene-1, rhodopsins, odorant, and cytomegalovirus receptors.

Most G-protein coupled receptors have single conserved cysteine residues in each of the first two extracellular loops, which form disulfide bonds that are believed to stabilize functional protein structure. The 7 transmembrane regions are designated as TM1, TM2, TM3, TM4, TM5, TM6, and TM7. TM3 has been implicated in signal transduction.

Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxy terminus. For several G-protein coupled receptors, such as the b-adrenoreceptor, phosphorylation by protein kinase A and/or specific receptor kinases mediates receptor desensitization.

For some receptors, the ligand binding sites of G-protein coupled receptors are believed to comprise hydrophilic sockets formed by several G-protein coupled receptor transmembrane domains, said socket being surrounded by hydrophobic residues of the G-protein coupled receptors. The hydrophilic side of each G-protein coupled receptor transmembrane helix is postulated to face inward and form a polar ligand binding site. TM3 has been implicated in several G-protein coupled receptors as having a ligand binding site, such as the TM3 aspartate residue. TM5 serines, a TM6 asparagine and TM6 or TM7 phenylalanines or tyrosines are also implicated in ligand binding.

G-protein coupled receptors can be intracellularly coupled by heterotrimeric G-proteins to various intracellular enzymes, ion channels and transporters. See Johnson et al., *Endoc. Rev.*, 1989, 10:317–331. Different G-protein α-subunits preferentially stimulate particular effectors to modulate various biological functions in a cell. Phosphorylation of cytoplasmic residues of G-protein coupled receptors have been identified as an important mechanism for the regulation of G-protein coupling of some G-protein coupled receptors. G-protein coupled receptors are found in numerous sites within a mammalian host.

Over the past 15 years, nearly 350 therapeutic agents targeting 7 transmembrane (7 TM) receptors or their ligands have been successfully introduced onto the market. This indicates that these receptors and their ligands have an established, proven history as therapeutic targets. Clearly, there is a need for identification and characterization of further receptors and ligands which can play a role in preventing, ameliorating or correcting dysfunctions or diseases, including, but not limited to, infections such as bacterial, fungal, protozoan and viral infections, particularly infections caused by HIV-1 or HIV-2; pain; cancers; anorexia nervosa; bulimia; cachexia; obesity; diabetes; asthma; Parkinson's disease; both acute and congestive heart failure; hypotension; hypertension; urinary retention; osteoporosis; angina pectoris; myocardial infarction; ulcers; asthma; allergies; benign prostatic hypertrophy; chronic renal failure; renal disease; impaired glucose tolerance; sexual dysfunction and psychotic and neurological disorders, including anxiety, schizophrenia, manic depression, delirium, dementia, severe mental retardation and dyskinesias, such as Huntington's disease or Gilles dela Tourett's syndrome, among others.

Polypeptides and polynucleotides encoding the human 7-transmembrane G-protein coupled neuropeptide receptor, HFGAN72, have been identified and are disclosed in. U.S. application Ser. No.: 08/846,704, now U.S. Pat. No. 6,020,157, granted on Feb. 1, 2000, and 08/846,705, now abandoned, both of which were filed on Apr. 30, 1997, as well as in WO 96/34877, published on Nov. 7, 1996.

The present invention provides polypeptides and polynucleotides encoding polypeptides which are ligands for the HFGAN72 receptor.

SUMMARY OF THE INVENTION

Toward these ends, and others, it is an object of the present invention to provide polypeptides, inter alia, that have been identified as ligands for the HFGAN72 receptor.

It is a further object of the invention, moreover, to provide polynucleotides encoding HFGAN72 receptor ligands.

In accordance with this aspect of the invention, there are provided methods using isolated HFGAN72 receptor ligand polypeptides and nucleic acid molecules encoding these receptor ligand polypeptides, including mRNAs, cDNAs, genomic DNAs and, in further embodiments of this aspect of the invention, biologically, diagnostically, clinically or therapeutically useful variants, analogs or derivatives thereof, or fragments thereof, including fragments of the variants, analogs and derivatives.

It is also an object of the invention to provide an agonist of the interaction of the HFGAN72 receptor ligands and the HFGAN72 receptor.

Another object of the invention is to provide an antibody against the interaction of the HFGAN72 receptor ligands and the HFGAN72 receptor.

A further object of the invention is an antagonist which inhibits the interaction of the HFGAN72 receptor ligands and the HFGAN72 receptor.

It is also an object of the invention to provide a method for the treatment of a patient having need of an HFGAN72 receptor ligand comprising administering to the patient a therapeutically effective amount of the ligand, wherein said patient is suffering from a disease or disorder, including, but not limited to, infections such as bacterial, fungal, protozoan and viral infections, particularly infections caused by HIV-1 or HIV-2; pain; cancers; anorexia nervosa; bulimia; cachexia; obesity; diabetes; asthma; Parkinson's disease; both acute and congestive heart failure; hypotension; hypertension; urinary retention; osteoporosis; angina pectoris; myocardial infarction; ulcers; asthma; allergies; benign prostatic hypertrophy; chronic renal failure; renal disease; impaired glucose tolerance; sexual dysfunction and psychotic and neurological disorders, including anxiety, schizophrenia, manic depression, delirium, dementia, severe mental retardation and dyskinesias, such as Huntington's disease or Gilles dela Tourett's syndrome, among others.

It is another object of the invention to provide a diagnostic process comprising analyzing for the presence of an HFGAN72 receptor ligand in a sample derived from a host suspected of having a disease or disorder, including, but not limited to, infections such as bacterial, fungal, protozoan and viral infections, particularly infections caused by HIV-1 or HIV-2; pain; cancers; anorexia nervosa; bulimia; cachexia; obesity; diabetes; asthma; Parkinson's disease; both acute and congestive heart failure; hypotension; hypertension; urinary retention; osteoporosis; angina pectoris; myocardial infarction; ulcers; asthma; allergies; benign prostatic hypertrophy; chronic renal failure; renal disease; impaired glucose tolerance; sexual dysfunction and psychotic and neurological disorders, including anxiety, schizophrenia, manic depression, delirium, dementia, severe mental retardation and dyskinesias, such as Huntington's disease or Gilles dela Tourett's syndrome, among others.

It is yet another object of the invention to provide a method for identifying compounds which bind to and activate or inhibit the interaction of HFGAN72 receptor ligands and the HFGAN72 receptor comprising contacting a cell expressing on the surface thereof an HFGAN72 receptor, said receptor being associated with a second component capable of providing a detectable signal in response to the binding of the HFGAN72 receptor ligands to said receptor, with a compound to be screened under conditions to permit binding to the receptor; and determining whether the compound binds to and activates or inhibits the interaction of the HFGAN72 receptor ligands and the HFGAN72 receptor by detecting the presence or absence of a signal generated from this interaction. In addition, the ligand can be labeled, for example with $^{125}I$, and used in receptor binding assays to identify antagonists or agonists that block binding.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

FIG. 1 shows a genomic sequence (SEQ ID NO: 1) encoding human HFGAN72 receptor ligands. Capital letters show exons (cDNA) (SEQ ID NO: 21).

FIG. 2 shows a deduced amino acid sequence (SEQ ID NO: 2), which comprises two different human HFGAN72 receptor ligands, Lig 72A (SEQ ID NO: 3, shown by dashes) and Lig 72B (SEQ ID NO: 4, shown by asterisks).

FIG. 3 shows a cDNA sequence (SEQ ID NO: 5) encoding rat HFGAN72 receptor ligands.

FIG. 4 shows a deduced amino acid sequence of rat HFGAN72 receptor ligands (SEQ ID NO: 6), which includes the N-terminal signal and leader sequence predicted with von Heijin's algorithm (SEQ ID NO: 7). Also shown in FIG. 4 are two ligands, Lig 72A (SEQ ID NO: 8, shown by dashes) and Lig 72B (SEQ ID NO: 9, shown by asterisks).

FIG. 5 shows a prepro region of an amino acid sequence of mouse HFGAN72 receptor ligands lacking a portion of the N-terminal signal sequence (SEQ ID NO: 10). This amino acid sequence comprises two ligands, Lig 72A (SEQ ID NO: 11, shown by dashes) and Lig 72B (SEQ ID NO: 12, shown by asterisks).

GLOSSARY

The following illustrative explanations are provided to facilitate understanding of certain terms used frequently herein, particularly in the examples. The explanations are provided as a convenience and are not meant to limit the invention.

"Isolated" means altered "by the hand of man" from its natural state; i.e., that, if it occurs in nature, it has been changed or removed from its original environment, or both. For example, a naturally occurring polynucleotide or a polypeptide naturally present in a living animal in its natural state is not "isolated," but the same polynucleotide or polypeptide separated from the coexisting materials of its natural state is "isolated" as the term is employed herein. For example, with respect to polynucleotides, the term isolated means that it is separated from the chromosome and cell in which it naturally occurs.

As part of or following isolation, such polynucleotides can be joined to other polynucleotides such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as a media, formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

"Oligonucleotide(s)" refers to relatively short polynucleotides. Often the term refers to single-stranded deoxyribonucleotides, but it can refer as well to single- or double-stranded ribonucleotides, RNA:DNA hybrids and double-stranded DNAs, among others.

"Polynucleotide(s)" generally refers to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide, as used herein, refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term polynucleotide also includes DNAs or RNAs as described above that contain one or more modified bases. Thus, DNAs or RNAs with backbones modified for stability or for other reasons are polynucleotides, as that term is intended herein. Moreover, DNAs or RNAs comprising unusual bases, such as inosine, or modified bases, such as tritylated bases, to name just two examples, are polynucleotides, as the term is used herein. It will be appreciated that a great variety of modifications have been made to DNA and RNA that serve many useful purposes known to those of skill in the art. The term polynucleotide, as it is employed herein, embraces such chemically, enzymatically or metabolically modified forms of polynucleotides, as well as the chemical forms of DNA and RNA characteristic of viruses and cells, including inter alia simple and complex cells.

"Polypeptides," as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types.

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, or by chemical modification techniques which are well known to the art. Even the common modifications that occur naturally in polypeptides are too numerous to list exhaustively here, but they are well described in basic texts and in more detailed monographs, as well as in a voluminous research literature, and thus are well known to those of skill in the art. Known modifications which may be present in polypeptides of the present invention include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature. Several particularly common modifications including glycosylation, lipid attachment, sulfation, gamma-carboxylation of glutamic acid residues, hydroxylation and ADP-ribosylation are described in most basic texts such as PROTEINS—STRUCTURE AND MOLECULAR PROPERTIES, 2nd Ed., T. E. Creighton, W. H. Freeman and Company, New York, 1993. Detailed reviews are also available on this subject. See e.g., Wold, F., Posttranslational Protein Modifications: Perspectives and Prospects, pages 1–12 in POST-TRANSLATIONAL COVALENT MODIFICATION OF PROTEINS, B. C. Johnson, Ed., Academic Press, New York, 1983; Seifter et al., "Analysis for protein modifications and nonprotein cofactors," *Meth. Enzymol.*, 1990, 182:626–646 and Rattan et al., "Protein Synthesis: Posttranslational Modifications and Aging," *Ann. N.Y. Acad. Sci.*, 1992, 663: 48–62.

It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural processes and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli*, prior to processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell's posttranslational modification capacity and the modification signals present in the polypeptide amino acid sequence. For instance, as is well known, glycosylation often does not occur in bacterial hosts such as *E. coli*. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to express efficiently mammalian proteins having the native patterns of glycosylation, inter alia. Similar considerations apply to other modifications.

It will be appreciated that the same type of modification may be present in the same or varying degrees at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

"Variant(s)" of polynucleotides or polypeptides, as the term is used herein, are polynucleotides or polypeptides that differ from a reference polynucleotide or polypeptide, respectively. Variants in this sense are described below and elsewhere in the present disclosure in greater detail.

Variants include polynucleotides that differ in nucleotide sequence from another, reference polynucleotide. Generally, differences are limited so that the nucleotide sequences of the reference and the variant are closely similar overall and, in many regions, identical.

As noted below, changes in the nucleotide sequence of the variant may be silent. That is, they may not alter the amino acids encoded by the polynucleotide. Where alterations are limited to silent changes of this type, a variant will encode a polypeptide with the same amino acid sequence as the reference. As also noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below.

Variants also include polypeptides that differ in amino acid sequence from another, reference polypeptide. Generally, differences are limited so that the sequences of the reference and the variant are closely similar overall and, in many regions, identical.

A variant and reference polypeptide may differ in amino acid sequence by one or more substitutions, additions, deletions, fusions and truncations, which may be present in any combination.

"Fusion protein" as the term is used herein, is a protein encoded by two, often unrelated, fused genes or fragments thereof. EP-AO464 533 (Canadian counterpart 2045869) discloses fusion proteins comprising various portions of constant region of immunoglobin molecules together with another human protein or part thereof. In many cases, employing an immunoglobulin Fc region as a part of a fusion protein is advantageous for use in therapy and diagnosis resulting in, for example, improved pharmacokinetic properties (EP-A 0232 262). On the other hand, for some uses it would be desirable to be able to delete the Fc part after the fusion protein has been expressed, detected and purified. Accordingly, it may be desirable to link the components of the fusion protein with a chemically or enzymatically cleavable linking region. This is the case when the Fc portion proves to be a hindrance to use in therapy and diagnosis, for example, when the fusion protein is to be used as an antigen for immunizations. In drug discovery, for example, human proteins, such as, shIL5-α have been fused with Fc portions for use in high-throughput screening assays to identify antagonists of hIL-5. See, D. Bennett et al., *Journal of Molecular Recognition*, 1995, 8:52–58; and K. Johanson et al., *The Journal of Biological Chemistry*, 1995, 270(16):9459–9471.

Thus, this invention also relates to genetically engineered soluble fusion proteins comprised of an HFGAN72 receptor ligand, or a portion thereof, and of various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In one embodiment, the Fc part can be removed simply by incorporation of a cleavage sequence which can be cleaved with blood clotting factor Xa. This invention further relates to processes for the preparation of these fusion proteins by genetic engineering, and to the use thereof for diagnosis and therapy. Yet a further aspect of the invention relates to polynucleotides encoding such fusion proteins.

"Binding molecules" (or otherwise called "interaction molecules" or "receptor component factors") refer to molecules, including receptors, that specifically bind to or interact with polypeptides of the present invention. Such binding molecules are a part of the present invention. Binding molecules may also be non-naturally occurring, such as antibodies and antibody-derived reagents that bind specifically to polypeptides of the invention.

As known in the art, "similarity" between two polypeptides is determined by comparing the amino acid sequence and its conserved amino acid substitutes of one polypeptide to the sequence of a second polypeptide. Moreover, also known in the art is "identity," which means the degree of sequence relatedness between two polypeptide or two polynucleotide sequences as determined by the identity of the match between two strings of such sequences. Both identity and similarity can be readily calculated (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov,. M. and Devereux, J., eds., M Stockton Press, New York, 1991). There exist a number of methods to measure identity and similarity between two polynucleotide or polypeptide sequences, and the terms "identity" and "similarity" are well known to skilled artisans (Carillo, H., and Lipton, D., SIAM *J. Applied Math.*, 1988, 48:1073). Methods commonly employed to determine identity or similarity between two sequences include, but are not limited to, those disclosed in GUIDE TO HUGE COMPUTERS, Martin J. Bishop, ed., Academic Press, San Diego, 1994, and Carillo, H., and Lipton, D., SIAM *J. Applied Math.*, 1988, 48:1073. Preferred methods to determine identity are designed to give the largest match between the two sequences tested. Methods to determine identity and similarity are also codified in computer programs. Preferred computer program methods to determine identity and similarity between two sequences include, but are not limited to, GCG program package (Devereux, J., et al., *Nucleic Acids Research*, 1984, 12(1):387), BLASTP, BLASTN, FASTA (Atschul, S. F. et al., *J. Molec. Biol.*, 1990, 215:403).

DETAILED DESCRIPTION OF THE INVENTION

In one aspect, the present invention relates to polypeptides and polynucleotides of novel HFGAN72 receptor ligands. These polypeptides include the polypeptides of a human HFGAN72 receptor ligand (SEQ ID NO: 2), a rat receptor ligand (SEQ ID NO: 6), and a mouse receptor ligand (SEQ ID NO: 10), the amino acid sequences of which are depicted in FIGS. 2 (SEQ ID NOs: 2–4), 4 (SEQ ID NOs: 6–9), and 5 (SEQ ID NOs: 10–12), respectively. The invention also relates to polypeptides comprising an amino acid sequence which is at least 80% identical to an amino acid sequence selected from the group consisting SEQ ID Nos: 2–4, 6, and 8–12 over its entire length, and still more preferably 90% identity, and even still more preferably at least 95–97% identity to these amino acid sequences.

Novel polypeptides of identical mass, which are ligands for the HFGAN72 receptor, were isolated from rat brain and bovine hypothalamus. The amino acid sequence of the mature rat polypeptide, Lig 72A, was determined and is shown in FIG. 4 as SEQ ID NO: 8. An accurate mass of the peptide MH+ ion was measured using delayed extraction MALDI and found to be 1286.6125 (calc. 1286.6237). The Gin residue at position 9 (see FIG. 3) was distinguished from Lys (both amino acids have the same residue mass) by acetylation of the peptide and re-measurement of the molecular weight. The molecular weight shifted by 42 Da from 1286.6 to 1328.6 (calc. 1328.6) thus indicating the addition of only one acetate group. Because Gin residues cannot be acetylated, and the N-terminus is blocked, the addition of only one acetate group strongly suggests the C-terminal sequence of a digested molecule is QK, not KK. Based upon the similarity in molecular weight, it is believed that the rat polypeptide has the same sequence.

Results from in situ hybridizations on adult rat brain slices show that the HFGAN72 receptor ligands are strongly expressed in both the hypothalamus and in the hypothalamal neurons. Because the HFGAN72 receptor ligands are localized in the hypothalamus, it is believed that they are involved in a number of neurological (e.g., epilepsy, stroke), psychiatric (e.g., anziety, depression), and/or eating disorders.

Interestingly, the amino acid sequences for Lig 72A are identical in the human (SEQ ID NO: 3), rat (SEQ ID NO: 8), and mouse (SEQ ID NO: 11). It was found that Lig 72B of the human (SEQ ID NO: 4), rat (SEQ ID NO: 9), and mouse (SEQ ID NO: 12) interact with the HFGAN72 receptor, and thus could have the same properties as Lig 72A.

The activity of the Lig 72A and Lig 72B for the HFGAN72 receptor were confirmed. Experiments were performed on Fura-loaded 293 cells transfected with the HFGAN72 receptor. Intracellular calcium levels were measured in the cells in response to increasing concentrations of polypeptides of the HFGAN72 receptor ligands, Lig 72A and Lig 72B. The $EC_{50}$ of the polypeptide was estimated to be 50 ng/ml. Activation of the HFGAN72 receptor by both Lig 72A and Lig 72B was determined to be specific, as no stimulation was observed with either 293pCDN vector transfected cells or with an alternative clone.

It is believed that HFGAN72 receptor ligands, or fragments, analogs and derivatives of these ligand polypeptides, may be useful in modulating HFGAN72 receptor activities. Thus, the present invention also relates to fragments, analogs and derivatives of these polypeptides. The terms "fragment," "derivative" and "analog" when referring to the polypeptide meansa polypeptide which retains essentially the same biological function or activity, i.e., functions as HFGAN72 receptor ligands, or retains the ability to bind any receptors or binding molecules even though the polypeptide may not activate the receptor in the same manner. Thus, an analog includes, for example, a proprotein which can be activated by cleavage of the proprotein portion to produce an active mature polypeptide or a portion of the HFGAN72 ligands.

The polypeptide of the present invention may be a recombinant polypeptide, a natural polypeptide or a synthetic polypeptide. In certain preferred embodiments, it is a recombinant polypeptide.

The fragment, derivative or analog of the polypeptide may be: (i) one in which one or more of the amino acid residues are substituted with a conserved or non-conserved amino acid residue (preferably a conserved amino acid residue) and such substituted amino acid residue may or may not be one encoded by the genetic code; (ii) one in which one or more of the amino acid residues includes a substituent group; (iii) one in which the mature polypeptide is fused with another compound, such as a compound to increase the half-life of the polypeptide (for example, polyethylene glycol); or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

Among preferred embodiments of the invention in this regard are polypeptides having the amino acid sequences of the HFGAN72 receptor ligands set out in FIGS. 2 (SEQ ID NOs: 2–4), 3 (SEQ ID NOs: 6, 8, and 9), and 4 (SEQ ID NOs: 10–12), and more particularly, the mature polypeptide, Lig 72A, set out in FIG. 2 as SEQ ID NO: 3, FIG. 4 as SEQ ID NO: 8, and FIG. 5 as SEQ ID NO: I1, variants, analogs, derivatives and fragments thereof, and variants, analogs and derivatives of the fragments. Further, particularly preferred embodiments of the invention in this regard are polypeptides, variants, analogs, derivatives and fragments thereof, and variants, analogs and derivatives of the fragments which retain the activity or function of Lig 72A and Lig 72B.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Iie; interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr.

Further, particularly preferred in this regard are variants, analogs, derivatives and fragments, and variants, analogs and derivatives of the fragments, having the amino acid sequence selected from the group consisting of the polypeptide in FIGS. 2 (SEQ ID NOs: 2–4), 4 (SEQ ID NOs: 6, 8, and 9), and 5 (SEQ ID NOs: 10–12), in which several, a few, 5 to 10 1 to 5, 1 to 3, 2, 1 or no amino acid residues are substituted, deleted or added, in any combination. Especially preferred among these are silent substitutions, additions and deletions, which do not alter the properties and activities of the ligands. Also especially preferred in this regard are conservative substitutions. Most highly preferred are polypeptides having the amino acid sequence selected from the group consisting of FIGS. 2 (SEQ ID NO: 2, SEQ ID NO: 3 or SEQ ID NO: 4), 4 (SEQ ID NO: 6, SEQ ID NO: 8 or SEQ ID NO: 9), and 5 (SEQ ID NO: 10, SEQ ID NO: 11 or SEQ ID NO: 12), without substitutions.

The polypeptides and polynucleotides of the present invention are preferably provided in an isolated form, and preferably are purified to homogeneity.

The polypeptides of the present invention include the polypeptides of SEQ ID NOs: 2–4, 6, and 8–12, and, in particular, the mature polypeptide selected from the group consisting of SEQ ID NOs: 4, 8, and 11, as well as polypeptides which have at least 80% identity to these polypeptides, and more preferably at least 90% similarity (more preferably at least 90% identity) to these polypeptides, and still more preferably, at least 95–97% similarity (still more preferably at least 95–97% identity) to these polypeptides.

Fragments or portions of the polypeptides of the present invention may be employed for producing the corresponding full-length polypeptide by peptide synthesis; therefore, the. fragments may be employed as intermediates for producing the full-length polypeptides. Fragments may be "freestanding," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragments of polypeptides of HFGAN72 receptor ligands of the present invention comprised within a precursor polypeptide designed for expression in a host and having heterologous pre- and pro-polypeptide regions fused to the amino terminus of the polypeptide fragments of HFGAN72 receptor ligands and an additional region fused to the carboxyl terminus of the fragment. Therefore, fragments in one aspect of the meaning intended herein, refers to the portion or portions of a fusion polypeptide or fusion protein derived from HFGAN72 receptor ligands.

Among especially preferred fragments of the invention are truncation mutants of HFGAN72 receptor ligands. Truncation mutants include polypeptides of the HFGAN72 receptor ligands having the amino acid sequence selected from the group consisting of FIGS. 2 (SEQ ID NOs: 2–4), 4 (SEQ ID NOs: 6, 8, and 9) and 5 (SEQ ID NOs: 10–12), or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspond to the preferred fragments, as discussed above, and most preferably SEQ ID NO: 21, as depicted in FIG. 1 or SEQ ID NO: 5, as depicted in FIG. 3.

Polypeptides of HFGAN72 receptor ligands and polynucleotides encoding these polypeptides may be used in accordance with the present invention for a variety of applications, particularly those that make use of the chemical and biological properties of these ligands. Additional applications relate to diagnosis and to treatment of disorders of cells, tissues and organisms. These aspects of the invention are illustrated further by the following discussion.

In one embodiment, the present invention relates to diagnostic assays including both qualitative and quantitative assays for detecting levels of HFGAN72 receptor ligands in cells, tissues, and biological fluids, including determination of normal and abnormal levels. Thus, for instance, a diagnostic assay in accordance with the invention for detecting over- or under-expression of the HFGAN72 receptor ligands compared to normal control tissue samples may be used to detect a susceptibility to a disease or disorder, including, but not limited to, infections such as bacterial, fungal, protozoan and viral infections, particularly infections caused by HIV-1 or HIV-2; pain; cancers; anorexia nervosa; bulimia; cachexia; obesity; diabetes; asthma; Parkinson's disease; both acute and congestive heart failure; hypotension; hypertension; urinary retention; osteoporosis; angina pectoris; myocardial infarction; ulcers; asthma; allergies; benign prostatic hypertrophy; chronic renal failure; renal disease; impaired glucose tolerance; sexual dysfunction and psychotic and neurological disorders, including anxiety, schizophrenia, manic depression, delirium, dementia, severe mental retardation and dyskinesias, such as Huntington's disease or Gilles dela Tourett's syndrome, among others. Assay techniques that can be used to determine levels of a protein, such as HFGAN72 receptor ligands of the present invention, in a sample derived from a host are well-known to those of skill in the art. Such assay methods include radioimmunoassays, competitive-binding assays, Western Blot analysis and enzyme linked immunosorbent assays (ELISA). Among these, ELISAs are frequently preferred. An ELISA assay initially comprises preparing an antibody specific to an HFGAN72 receptor ligand, preferably a monoclonal antibody. In addition a reporter antibody generally is prepared which binds to the monoclonal antibody. The reporter antibody is attached to a detectable reagent such as radioactive, fluorescent or enzymatic reagent.

To carry out an ELISA, a sample is removed from a host and incubated on a solid support, e.g., a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any HFGAN72 receptor ligands attached to the polystyrene dish. Unbound monoclonal antibody is washed out with buffer. The reporter antibody linked to horseradish peroxidase is placed in the dish resulting in binding of the reporter antibody to any monoclonal antibody bound to HFGAN72 receptor ligands. Unattached reporter antibody is then washed out. Reagents for peroxidase activity, including a colorimetric substrate are then added to the dish. Immobilized peroxidase, linked to HFGAN72 receptor ligands through the primary and secondary antibodies, produces a colored reaction product. The amount of color developed in a given time period indicates the amount of ligand present in the sample. Quantitative results typically are obtained by reference to a standard curve.

A competition assay may be employed wherein antibodies specific to an HFGAN72 receptor ligand attached to a solid support and labeled HFGAN72 receptor ligand and a sample derived from the host are passed over the solid support. The amount of detected label attached to the solid support can be correlated to a quantity of HFGAN72 receptor ligand in the sample.

Methods of producing antibodies useful in these assays are well known to those skilled in the art. Polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of a Fab expression library. Various procedures known in the art may be used for the production of such antibodies and fragments.

Antibodies generated against the polypeptides corresponding to a sequence of the present invention can be obtained by direct injection of the polypeptides into an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler, G. and Milstein, C., Nature, 1975, 256: 495–497, the trioma technique, the human B-cell hybridoma technique (Kozbor et al., Immunology Today, 1983, 4: 72 (1983) and the EBV-hybridoma technique to produce human monoclonal antibodies (Cole et al., pages 77–96 in MONOCLONAL ANTIBODIES AND CANCER THERAPY, Alan R. Liss, Inc. (1985)).

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express humanized antibodies to immunogenic polypeptide products of this invention.

The above-described antibodies may be employed to isolate or to identify clones expressing the polypeptide or purify the polypeptide of the present invention by attachment of the antibody to a solid support for isolation and/or purification by affinity chromatography.

In addition, antibodies against an HFGAN72 receptor ligand may be employed to inhibit interaction of such a ligand with the HFGAN72 receptor and may be useful in the treatment of diseases or disorders, including, but not limited to, infections such as bacterial, fungal, protozoan and viral infections, particularly infections caused by HIV-1 or HIV-2; pain; cancers; anorexia nervosa; bulimia; cachexia; obesity; diabetes; asthma; Parkinson's disease; both acute and congestive heart failure; hypotension; hypertension; urinary retention; osteoporosis; angina pectoris; myocardial infarction; ulcers; asthma; allergies; benign prostatic hypertrophy; chronic renal failure; renal disease; impaired glucose tolerance; sexual dysfunction and psychotic and neurological disorders, including anxiety, schizophrenia, manic depression, delirium, dementia, severe mental retardation and dyskinesias, such as Huntington's disease or Gilles dela Tourett's syndrome, among others.

HFGAN72 receptor ligands could be used to isolate proteins which interact with it and, this interaction could be a target for interference. Inhibitors of protein-protein interactions between HFGAN72 receptor ligands and other factors could lead to the development of pharmaceutical agents for the modulation of HFGAN72 receptor ligand activity. As used herein, the term "modulate" refers to affecting the HFGAN72 receptor ligand function.

Thus, this invention also provides a method for identification of binding molecules to HFGAN72 receptor ligands. Genes encoding proteins for binding molecules to HFGAN72 receptor ligands can be identified by numerous methods known to those of skill in the art, for example, ligand panning and FACS sorting. Such methods are described in many laboratory manuals such as, for instance, Coligan et al., Current Protocols in Immunology 1 (kivett, A. J. Biochem. J. 291:1–10(1993)): Chapter5 (1991).

For example, the yeast two-hybrid system provides methods for detecting the interaction between a first test protein and a second test protein, in vivo, using reconstitution of the activity of a transcriptional activator. The method is disclosed in U.S. Pat. No. 5,283,173; reagents are available from Clontech and Stratagene. Briefly, cDNA of an HFGAN72 receptor ligand is fused to a Gal4 transcription factor DNA binding domain and expressed in yeast cells. cDNA library members obtained from cells of interest are fused to a transactivation domain of Gal4. cDNA clones which express proteins which can interact with an HFGAN72 receptor ligand will lead to reconstitution of Gal4 activity and transactivation of expression of a reporter gene such as Gal1-lacZ. The cDNA of the HFGAN72 receptor ligand which is fused to the Gal4 transcription factor DNA binding domain may be mutated in one or more amino acids, the method of which is described above, to enhance interaction of kinase with substrate.

An alternative method is screening of λgt11, λZAP (Stratagene) or equivalent cDNA expression libraries with recombinant HFGAN72 receptor ligands. Recombinant HFGAN72 receptor ligand protein or fragments thereof are fused to small peptide tags such as FLAG, HSV or GST. The peptide tags can possess convenient phosphorylation sites for a kinase such as heart muscle creatine kinase or they can be biotinylated. Recombinant HFGAN72 receptor ligands can be phosphorylated with 32[P] or used unlabeled and detected with streptavidin or antibodies against the tags. λgt11cDNA expression libraries are made from cells of interest and are incubated with the recombinant HFGAN72 receptor ligands, washed and cDNA clones isolated which interact with the HFGAN72 receptor ligands. See, e.g., T. Maniatis et al, supra.

Another method is the screening of a mammalian expression library in which the cDNAs are cloned into a vector between a mammalian promoter and polyadenylation site and transiently transfected in COS or 293 cells followed by detection of the binding protein 48 hours later by incubation of fixed and washed cells with a labelled HFGAN72 receptor ligand, preferably iodinated, and detection of bound HFGAN72 receptor ligands by autoradiography. See Sims et al., *Science* 241:585–589 (1988) and McMahan et al., *EMBO J.* 10:2821–2832 1991). In this manner, pools of cDNAs containing the cDNA encoding the binding protein of interest can be selected and the cDNA of interest can be isolated by further subdivision of each pool followed by cycles of transient transfection, binding and autoradiography. Alternatively, the cDNA of interest can be isolated by transfecting the entire cDNA library into mammalian cells and panning the cells on a dish containing an HFGAN72 receptor ligand bound to the plate. Cells which attach after washing are lysed and the plasmid DNA isolated, amplified in bacteria, and the cycle of transfection and panning repeated until a single cDNA clone is obtained. See Seed et al., *Proc. Natl. Acad. Sci. USA* 84:3365 (1987) and Aruffo et al., *EMBO J*. 6:3313 (1987). If the binding protein is secreted, its cDNA can be obtained by a similar pooling strategy once a binding or neutralizing assay has been established for assaying supernatants from transiently transfected cells. General methods for screening supernatants are disclosed in Wong et al., *Science* 228:810–815 (1985).

Another alternative method is isolation of proteins interacting with an HFGAN72 receptor ligand directly from cells. Fusion proteins of an HFGAN72 receptor ligand with GST or small peptide tags are made and immobilized on beads. Biosynthetically labeled or unlabeled protein extracts from the cells of interest are prepared, incubated with the beads and washed with buffer. Proteins interacting with an HFGAN72 receptor ligand are eluted specifically from the beads and analyzed by SDS-PAGE. Binding partner primary amino acid sequence data are obtained by microsequencing. Optionally, the cells can be treated with agents that induce a functional response such as tyrosine phosphorylation of cellular proteins. An example of such an agent would be a growth factor or cytokine such as interleukin-2.

Another alternative method is immunoaffinity purification. A recombinant HFGAN72 receptor ligand is incubated with labeled or unlabeled cell extracts and immunoprecipitated with anti-HFGAN72 receptor ligand antibodies. The immunoprecipitate is recovered with protein A-Sepharose and analyzed by SDS-PAGE. Unlabelled proteins are labeled by biotinylation and detected on SDS gels with streptavidin. Binding partner proteins are analyzed by microsequencing. Further, standard biochemical purification steps known to those skilled in the art may be used prior to microsequencing.

Yet another alternative method is screening of peptide libraries for binding partners. A recombinant tagged or labeled HFGAN72 receptor ligand is used to select peptides from a peptide or phosphopeptide library which interact with an HFGAN72 receptor ligand. Sequencing of the peptides leads to identification of consensus peptide sequences which might be found in interacting proteins.

In summary, HFGAN72 receptor ligand binding partners identified by any of these methods or other methods which would be known to those of ordinary skill in the art, as well as those putative binding partners discussed above, can be used in the assay method of the invention. Assaying for the presence of an HFGAN72 receptor ligand/binding partner complex are accomplished by, for example, the yeast two-hybrid system, ELISA or immunoassays using antibodies specific for the complex. In the presence of test substances (i.e., inhibitors or antagonists) which interrupt or inhibit formation of HFGAN72 receptor ligand/binding partner interaction, a decreased amount of complex will be determined relative to a control lacking the test substance.

Polypeptides of the invention also can be used to assess HFGAN72 receptor ligand bing capacity of HFGAN72 receptor ligand binding molecules in cells or in cell-free preparations.

The HFGAN72 receptor ligands of the present invention can also be employed in a process for screening for compounds which activate (agonists) or inhibit (antagonists) the ligand's activation of the HFGAN72 receptor.

In general, such screening procedures involve providing appropriate cells which express the HFGAN72 receptor on the surface thereof. Such cells include cells from mammals, yeast, Drosophila or *E. coli*. In particular, a polynucleotide encoding the HFGAN72 receptor is employed to transfect cells to thereby express the receptor. The expressed receptor is then contacted with a test compound and an HFGAN72 receptor ligand of the present invention to observe binding, stimulation or inhibition of a functional response.

One such screening procedure involves the use of melanophores which are transfected to express the HFGAN72 receptor. Such a screening technique is described in WO 92/01810, published Feb. 6, 1992.

Thus, for example, such assay may be employed for screening for a compound which inhibits interaction of the ligand with the HFGAN72 receptor by contacting melanophore cells which encode the receptor with both an HFGAN72 receptor ligand of the present invention and a compound to be screened. Inhibition of the signal generated by the ligand indicates that a compound is a potential antagonist for the receptor, i.e., inhibits activation of the receptor by HFGAN72.

The screen may be employed for determining a compound which activates the receptor by contacting such cells with compounds to be screened and determining whether such compound generates a signal, i.e., activates the receptor, resulting in a second messenger response such as, but not limited to, cAMP inhibition or stimulation, calcium mobilization, and GTPγS binding.

Another such screening technique involves introducing RNA encoding the FGAN72 receptor into Xenopus oocytes to transiently express the receptor. The receptor oocytes may then be contacted with a receptor ligand of the present invention and a compound to be screened, followed by detection of inhibition or activation of a signal in the case of screening for compounds which are thought to inhibit activation of the receptor by the ligand.

Another method involves screening for compounds which inhibit activation of the receptor by determining inhibition of binding of labeled an HFGAN72 receptor ligand of the present invention to cells which have the receptor on the surface thereof. Such a method involves transfecting a eukaryotic cell with DNA encoding the HFGAN72 receptor such that the cell expresses the receptor on its surface and contacting the cell or cell membrane preparation with a compound in the presence of a labeled form of an HFGAN72 receptor ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

Yet another screening technique involves the use of FLIPR equipment for high throughput screening of test compounds that inhibit mobilization of intracellular calcium ions, or other ions, by affecting the interaction of an HFGAN72 receptor ligand with the HFGAN72 receptor.

HFGAN72 receptors are found in the mammalian host and, thus, may be responsible for many biological functions, including many pathologies. Accordingly, it is desirous to find compounds which stimulate the HFGAN72 receptor or the interaction of HFGAN72 receptor ligands and the HFGAN72 receptor, on the one hand, and which can inhibit the function of the HFGAN72 receptor, on the other hand.

For example, the HFGAN72 receptor has been preliminarily demonstrated to be upregulated in vascular smooth muscle cells treated with serum, down-regulated in macrophages treated with oxidized LDL and has also been found in stented arteries. Accordingly, modulation of the activity of this receptor with polypeptides or fragments, derivatives or variants of the polypeptides of the instant invention may be useful in treating cardiovascular disorders. Isolation of this ligand from the brain and hypothalamus is also indicative of CNS relevance. Thus, the present invention also relates to methods of using an HFGAN72 receptor ligand or compounds which modulate the interaction of such a ligand with the HFGAN72 receptor in the treatment of patients suffering from diseases or disorders, including, but not limited to, infections such as bacterial, fungal, protozoan and viral infections, particularly infections caused by HIV-1 or HIV-2; pain; cancers; anorexia nervosa; bulimia; cachexia; obesity; diabetes; asthma; Parkinson's disease; both acute and congestive heart failure; hypotension; hypertension; urinary retention; osteoporosis; angina pectoris; myocardial infarction; ulcers; asthma; allergies; benign prostatic hypertrophy; chronic renal failure; impaired glucose tolerance; sexual dysfunction and psychotic and neurological disorders, including anxiety, schizophrenia, manic depression, delirium, dementia, severe mental retardation and dyskinesias, such as Huntington's disease or Gilles dela Tourett's syndrome, among others.

Example 5 shows that central administration of Lig 72A (SEQ ID NO: 8) stimulated food intake in freely-feeding rats during a 4 hour time period. This increase was approximately four-fold over control rats receiving vehicle. These data suggest that Lig 72A may be an endogenous regulator of appetite. Therefore, antagonists of its receptor may be useful in the treatment of obesity and diabetes, while agonists or antagonists may be useful in the treatment of eating disorders such as anorexia nervosa, bulimia, and cachexia, among others.

Moreover, Example 6 shows that Lig 72A (SEQ ID NO: 8) induced antidiuresis when infused intravenously in the conscious rat, without affecting systemic or renal hemodynamics. These data also suggest that an HFGAN72 receptor antagonist would possess novel diuretic activity and, therefore, may be useful in the treatment of chronic renal failure, Type II diabetes, renal disease, congestive heart failure, impaired glucose tolerance, obesity, and sexual dysfunction, among others.

Thus, the present invention also relates to compositions comprising the polypeptides discussed above or the agonists or antagonists. Thus, the polypeptides of the present invention, or agonists or antagonists thereto, may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration.

The invention further relates to pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

Polypeptides and other compounds of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

The pharmaceutical compositions generally are administered in an amount effective for treatment or prophylaxis of a specific indication or indications. In general, the compositions are administered in an amount of at least about 10 µg/kg body weight. In most cases they will be administered in an amount not in excess of about 8 mg/kg body weight per day. Preferably, in most cases, dose is from about 10 µg/kg to about 1 mg/kg body weight, daily. It will be appreciated that optimum dosage will be determined by standard methods for each treatment modality and indication, taking into account the indication, its severity, route of administration, complicating conditions and the like.

EXAMPLES

Biological Methods

Certain terms used herein are explained in the foregoing glossary.

All examples were carried out using standard techniques, which are well known and routine to those of skill in the art, except where otherwise described in detail. Routine molecular biology techniques of the following examples can be carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989), herein referred to as "Sambrook."

Example 1

Cloning Method for the HFGAN72 Receptor Ligands a. Cloning Method for the Rat HFGAN72 Receptor Ligands:

Intrapeptide degenerate RT-PCR method was used to obtain the full-length sequence for the rat HFGAN72 receptor ligand.

The peptide sequence QPLPDCCRQKTCSCRLYELLH-GAGNHAGI (amino acids 1–29 of SEQ ID NO: 6) was chosen to design highly degenerate oligonucleotide primers encoding its ends. The sequences of primers were: CAAC-CNCTNCCNGACTGCTG (SEQ ID NO: 13) and ATNC-CNGCNGCATGATT (SEQ ID NO: 14). At position 3 of the primer of SEQ ID NO: 13, A can be substituted with G. At position 7 of the primer of SEQ ID NO: 13, C can be substituted with T. At position 15 of the primer of SEQ ID NO: 8, C can be substituted with T. At position 18 of SEQ ID NO: 13, C can be substituted with T. At position 12 of the primer of SEQ ID NO: 14, A can be sunstituted with G. At position 15 of the primer of SEQ ID NO: 14, A can be substituted with G. Any of all of these substitutions may be present in the primers of SEQ ID Nos: 13 and 14. In the nucleotide sequences of the above primers, the symbol "N" can be an A, C, G or T. The cDNA fragment encoding the peptide was obtained by RT-PCR from rat brain RNA and confirmed by nucleotide sequencing.

5'-RACE:

A non-degenerate oligonucleotide primer was designed (#1; GTTGCCAGCTCCGTGCAACAGTTCGTAGAGACGG) (SEQ ID NO: 15), based on the sequence of the above RT-PCR product, and used in a 5'-RACE reaction: Double stranded cDNA was synthesized from rat brain polyA+ RNA, ligated to the Marathon adaptor (Clontech), and used as template for the initial 5'-RACE reaction with the adaptor primer 1 (Clontech) and #1 as primers. A nested PCR reaction was performed with an oligonucleotide CGGCAG-GAACACGTCTTCTGGCG (#2) (SEQ ID NO: 16) and adaptor primer 2. An approx 250-bp 5' cDNA product, which correctly encodes the peptide, was obtained.

3'-RACE:

Two additional oligonucleotides were designed, TCCT-TGGGTATTTGGACCACTGCACCGAAG (#3) (SEQ ID NO: 17) and ATACCATCTCTCCGGATTGCCTCTC-CCTGA (#4) (SEQ ID NO: 18), which corresponded to a part of the putative 5'-noncoding region of the cDNA sequence obtained by the 5'-RACE reaction above. Single stranded rat brain cDNA was synthesized using an oligo-nucleotide CCTCTGAAGGTTCCAGAATCGATAGTAN (SEQ ID NO: 19) as a specific primer for the reverse transcription, and used as template for a 3'-RACE reaction using #3 and an anchor primer (CCTCTGAAGGTTCCAGAATCGATAG) (SEQ ID NO: 20). At position 27 of the oligonucleotide of SEQ ID NO: 19, A can be substituted with either C or G. In the nucleotide sequence of the oligonucleotide of SEQ ID NO: 19, the symbol "N" can be an A, C, G or T. The product was subjected to nested PCR reaction using #4 and the same anchor primer. A discrete 0.6-kb product containing the correct 5' cDNA sequence was obtained. The full-length sequence was confirmed on cDNA products obtained from three independent initial 3'-RACE reactions.

b. Cloning Method for the Human and Mouse HFGAN72 Receptor Ligands:

Approximately 1.2 million plaques each from human (Clontech) and mouse (Stratagene) genomic libraries were screened by standard plaque hybridization. A full-length (about 0.5 kb) rat cDNA insert encoding both HFGAN72 receptor ligands, Lig 72A and Lig 72B, was 32P-labeled by the random priming method and was used as a probe. Hybridization-positive phages were plaque-purified, and genomic DNA fragments containing exons of HFGAN72 receptor ligands were identified by Southern blotting and subcloned into plasmid vectors for further analyses. The complete nucleotide sequence of the genomic fragment was assembled from sequences of the overlapping subclones and sequences obtained by primer walking.

Example 2

Purification of HFGAN72 receptor ligands

About 220 grams of frozen bovine hypothalamus tissue or frozen rat brain tissue, purchased from Pel-Freez (Rogers, AR), were homogenized by Polytron (15-mm diameter) in 10×volume of 70% (volume/volume) acetone/1M acetic acid/20 mM HCl at room temperature. Homogenates were stored at 4° C. overnight to precipitate large proteins.

On the following day, the homogenates were centrifuged at 20,000×g for 30 minutes at 4° C. The centrifugation was repeated until all visible insoluble materials were removed from the supernatant. The supernatant was then aliquoted into several large glass bottles, and an equal volume of diethyl ether was added to each bottle. The mixture was vigorously shaken for 1–2 minutes, and the two phases were allowed to separate for 30 minutes at room temperature. The lower aqueous phase (which appears turbid) was transferred to fresh bottles, and the ether extraction was repeated two more times to remove any acetone. Following the extractions, the aqueous phase was centrifuged at 20,000×g for 30 minutes at 4° C. The supernatant was spun again to remove all insoluble materials. The final supernatant (approximately 500–600 ml) was then filtered through a mesh filter (Falcon Cell Strainer, Becton Dickinson, Co., Oxnard, Calif.) into a glass bottle. The filtrate was then diluted with an equal volume of $H_2O$ at room temperature and directly loaded onto two 10-gram cartridges of SepPak C18 (total of 20 gram bed), that were pre-equilibrated with 0.1% (volume/volume) trifluoroacetic acid (TFA). By apply-ing a gentle vacuum to the cartridges, flow rate was main-tained so that the individual droplets from the cartridge outlet were still visible. Each cartridge was washed with 100 ml of 5% $CH_3CN$/0.1% TFA, and then eluted with 30 ml of 50% $CH_3CN$/0.1% TFA. The first 6 milliliters of eluate was discarded as void. The remaining eluate was lyophilized in siliconized glass flask overnight.

The lyophilized material was dissolved in 24 milliliters of 1 M acetic acid by sonicating for 10–20 minutes or until there was no visible insoluble materials. The extract was then filtered through a 20-micron Mirex GV syringe filter (Millipore, Bedford, Mass.). Half (12 milliliters) of the filtered extract was directly loaded onto a C18 reverse-phase HPLC column (Vydac 218TP510; 5 micron; 10 mm×250 mm semiprep; Hesperia, Calif.), pre-equilibrated with 3% $CH_3CN$/0.1% TFA at a flow rate of 3 milliliters/minute at room temperature. Sample was loaded in four 3-milliliter boluses via a large (5 milliliter or greater) sample loop. A 10%–40% gradient of $CH_3CN$ in 0.1% TFA was then applied over 100 minutes. Three milliliter (or 1 minute) fractions were collected into siliconized 5 milliliter glass tubes. The identical HPLC was repeated once more for the remaining half of the extract. Sixty microliters (1/50) from each fraction were set aside and assayed for the Ca transients as described in Example 2, on 293/HFGAN72 cells.

The active fractions were pooled, and directly applied to a cation-exchange HPLC column (TosoHaas SP-5PW; 7.5 mm×75 mm; Montgomeryville, Pa.), pre-equilibrated with 20 mM Na-phosphate (pH 3.0)/30% $CH_3CN$ at room tem-perature. A 0–0.5 M gradient of NaCl in 20 mM Na-phosphate (pH 3.0)/30% $CH_3CN$ was applied over 60 minutes at a flow rate of 1 milliliter/minute. One milliliter fractions were collected, and 30 microliters from each fraction were used for the Ca assay.

The active fractions (2–3 fractions; 2–3 milliliter) were pooled, and diluted 4-fold with 0.1% TFA. The diluted sample was directly loaded onto an analytical C1 8 reverse-phase column (Vydac 218TP54; 4.6 mm×250 mm), pre-equilibrated with 3% $CH_3CN$/0.1% TFA at a flow rate of 1 milliliter/minute. The column was maintained at 40° C. with a column heater. A 21%–36% gradient of $CH_3CN$ in 0.1% TFA was applied over 75 minutes. Individual peaks (monitored at 210-nm absorption) were collected manually into siliconized 5 milliliter glass tubes, and 30 microliters from each fraction were assayed. At this point, the active peak was already >70–80% pure.

The active peak (about 1 milliliter) was diluted 4-fold with 0.1% TFA, and directly loaded onto the same C18 column, but this time pre-equilibrated with 3% $CH_3CN$/20 mM Tris-HCl (pH 7.0 at 40° C.). A 3%–40% gradient of $CH_3CN$ in 20 mM Tris-HCl (pH 7.0) was applied over 74 minutes at 40° C. The major 210-nm peak was collected manually.

At this point, the sample should already be pure. In order to confirm purity, as well as to desalt the material, the active peak (about 800 microliters) was diluted 4-fold with 0.1% TFA, and directly loaded onto a C8 reverse-phase column (Vydac 228TP104; pH-stable coated C8; 4.6 mm×250 ml), pre-equilibrated with 3% $CH_3CN$/0.1% TFA at a flow rate of 1 milliliter/minute. A 3%–36% gradient of $CH_3CN$ in 0.1% TFA was applied over 66 minutes at 40° C. The single 210-nm peak was collected manually. The biological activity was confirmed. The above process that was used to purify Lig 72A.

Lig 72B was found and purified by synthesizing the peptide based on the cDNA sequence and testing the synthesized product.

Example 3

Ca Assay for Lig72A and Lig 72B

The Ca assay was performed in accordance with procedures described by Sakuri et al., *Nature* 1990, 348:732–735. For the assay, a small portion of each HPLC fraction was transferred to a siliconized 1.5 milliliter Eppendorf tube and evaporated to dryness under vacuum. Dried material was reconstituted in 20 microliters of the Ca assay buffer (140 mM NaCl, 4 mM KCl, 1 mM $Na_2HPO_4$/1 mM $MgCl_2$, 1.25 mM $CaCl_2$, 11 mM glucose, 5 mM HEPES (pH 7.4) and 0.2% bovine serum albumin) by vortexing for 3 minutes. For each assay point, 10 microliters of the reconstituted solution was used. Cells were loaded with Fura-2/AM in accordance with standard procedures. A Jasco CAF-110 intracellular ion analyzer (Easton, Md.) with 0.5 ml assay cuvettes was used. The 293/HFGAN72 cells and non-transfected 293 cells were used in parallel to ensure the specificity of the response. Endothelin-1 (final concentration of 1–100 nM) was used as positive-control ligand.

Example 4

Determination of Amino Acid Sequences of Lig 72A and Lig 72B

A Lys-C digest of the reduced and alkylated Lig 72A in 50 mM Tris buffer, pH 9.0, was used for sequence analysis. One half of the sample (approximately 25 microliters) was purified and concentrated on a microcolumn packed with Poros RII resin. The peptides were eluted with 2 microliters of 70% methanol, 5% formic acid and transferred to a nano-electrospray needle. The sample was analyzed using nano-electrospray ionization on a PE-Sciex triple quadrupole mass spectrometer. A single peptide with a molecular weight of 1286.6 was observed. This peptide was sequenced using collision induced dissociation (CID) tandem mass spectrometry (MS/MS). In order to facilitate interpretation of the data, fragments of the peptide were also generated in the electrospray source which were subsequently sequenced by CID tandem MS (a technique referred to as $MS^3$). The fragments which were generated differed from one another by the loss of successive N-terminal amino acids beginning with the des 3 peptide fragment and continuing through the des 5 fragment.

Lig 72B was identified by direct Edman sequencing using an Hewlett Packard G1000A protein sequencer equipped with on-line Pth (phenylthiohydantoin) amino acid analysis. The molecular weight of the peptide was determined as 2935.9 Da by matrix-assisted laser desorption ionization mass spectrometry (MALDI-MS), indicating that the processed peptide was full length and amidated at the C-terminal residue.

Example 5

Lig 72A Rat Feeding Study

Using standard procedures, surgical implantation of a cannula into the left lateral ventricle of male Sprague Dawley rats was carried out using a stereotaxic frame. The position of each cannula was verified using a submaximal dose (2.35 nmol.) of porcine neuropeptide Y (NPY), a peptide which is known to stimulate feeding in rats and can be used as a positive control in feeding experiments. Subsequently, 9 rats received 3 doses of Lig 72A (2.34, 7.02, and 23.4 nmol.) in random order over a 2 week period. Food intake was measured hourly for the first two hours and again at 4 hours, and body weight was monitored on a daily basis.

Results show that Lig 72A stimulated food intake in freely-feeding rats over a 4 hour time period. The increase was approximately four-fold over control rats receiving vehicle. All doses of Lig 72A gave the same response, suggesting that even 2.34 nmols. is at the top of the dose response curve, and that lower doses need to be investigated to obtain further information on potency. The response duration for Lig 72A appeared to be longer than that for NPY. These data suggest that Lig 72A may be an endogenous regulator of appetite, and that antagonists of its receptor may be useful in the treatment of obesity and diabetes, whilst agonists or antagonists may be useful in the treatment of eating disorders such as anorexia nervosa, bulimia, and cachexia, among others.

Example 6

Antidiuretic Effects of Lig 72A in the Conscious Rat

The effects of Lig 72A on arterial blood pressure (MAP), heart rate (HR), renal blood flow (RBF) and glomerular filtration rate (GFR), as well as on the excretion of solutes and water by the kidneys were determined in conscious, chronically instrumented, male Sprague-Dawley (390–440 g) rats (n=5). Details of surgery and chronic care have been published earlier (Kidney Int. 15:419–426, 1979). Briefly, under anesthesia, catheters were implanted into the abdominal aorta and inferior vena cava via the femoral vessels. In addition, a silastic-covered stainless steel cannula was sewn into the urinary bladder. During recovery (6–8 days), rats were housed individually, had free access to food and water and were accustomed to a plastic restrainer.

During experiment periods, the rats were placed in a restrainer and connections were made for the recording of blood pressure and heart rate and collection of urine. Throughout the experiment, isotonic saline containing 10% inulin and 2% PAH was infused i.v. at a rate of 20 ul/min. A one hour equilibration was followed by two 20 min. urine collections (control). One blood sample was taken in the middle of the second collection, and then, Lig 72A was infused i.v. at a rate of 1 ug/kg/min for 90 min, during which time three 30 min. urine collections were performed, and another blood sample was taken between the second and third period.

Urinary and plasma concentrations of inulin and PAH were determined by spectrophotometry and electrolytes were measured by a Synchron AS8 Clinical Analyzer (Beckman Instrument Inc., Brea, Calif.). Glomerular filtration rate (GFR) was estimated from the renal clearance of inulin, renal plasma flow (RPF) as the clearance of PAH, renal blood flow (RBF) as RPF/(1-hematocrit). Clearance and excretion rates were calculated using standard procedures and are expressed per 100 g body weight. All values represent maximal changes, expressed as absolute values, and reported as group means±SEM. Statistical analyses were performed by using analysis of variance (ANOVA). A value of $P<0.05$ was considered statistically significant.

Control blood pressure was: $119\pm3.2$ mmHg, heart rate was: $405\pm9.9$ beats/min., and neither function was altered by Lig 72A. GFR and RBF increased moderately (not significantly), from $923\pm80$ to $1032\pm103$ and $5444\pm410$ to $6385\pm910$ ul/min/100 g, respectively, during the infusion of the peptide. In contrast, major changes were elicited by Lig 72A in: urine flow, from $22\pm3$ to $8.2\pm1.5$ ul/min/100 g ($p<0.05$); fractional excretion of sodium and potassium, from $1.58\pm0.3$ to $0.78\pm0.2$ and from $46\pm6$ to $32\pm2\%$ ($p<0.05$), respectively. The changes in clearance of osmoles (from $39\pm4$ to $30.3\pm3$ ul/min/100 g) and free water (from $-17.3\pm2$ to $-22.1\pm2$ ul/min/100 g) were not statistically significant.

The results indicate that Lig 72A induces antidiuresis when infused intravenously in the conscious rat, without affecting systemic or renal hemodynamics. These data also suggest that an HFGAN72 receptor antagonist would possess novel diuretic (natriuretic) activity and, therefore, may be useful in the treatment of chronic renal failure, Type II diabetes, renal disease, congestive heart failure, impaired glucose tolerance, obesity, and sexual dysfunction, among others.

---

What is claimed is:

1. A method for identifying a compound as an agonist or antagonist of the interaction between SEQ ID NO: 3 with the human HFGAN72 receptor, said method comprising the steps of:
   (a) in the presence of a labeled or unlabeled SEQ ID NO: 3, contacting a cell expressing on the surface thereof said human HFGAN72 receptor with said compound, said cell may be-associated with a second component capable of providing a detectable signal in response to the binding of SEQ ID NO: 3 to said receptor compared with cells' expressing on the surface thereof fewer or no human HFGAN72 receptors; and
   (b) determining whether said compound activates or inhibits said signal, wherein a compound that activates said signal is an agonist and a compound that inhibits said signal is an antagonist.

2. A method for identifying a compound as an agonist or antagonist of the interaction between SEQ ID NO: 3 with the human HFGAN72 receptor, said method comprising the steps of:
   (a) in the presence of a labeled or unlabeled SEQ ID NO: 3, contacting a cell expressing on the surface thereof said human HFGAN72 receptor with said compound, said cell may be associated with a second component capable of providing a detectable signal in response to the binding of SEQ ID NO: 3 to said receptor compared with cells expressing on the surface thereof fewer or no human HFGAN72 receptors; and
   (b) determining whether said compound causes a reduction in the binding of SEQ ID NO: 3 and said HFGAN72 receptor, wherein a compound that causes a reduction in said binding is either an agonist or antagonist.

* * * * *

SEQUENCE LISTING (1) GENERAL INFORMATION:

(iii) NUMBER OF SEQUENCES: 21

(2) INFORMATION FOR SEQ ID NO: 1:

(i) SEQUENCE CHARACTERISTICS:
      (A) LENGTH: 1970 base pairs
      (B) TYPE: nucleic acid
      (C) STRANDEDNESS: single
      (D) TOPOLOGY: linear (ii) MOLECULE TYPE: Genomic DNA (xi) SEQUENCE DESCRIPTION: SEQ ID NO: 1:

```
AAAACATAAT GTGGGTCTCG CGTCTGCCTC TCTCCCGCCC CTAATTAGCA GCTGCCTCCC      60

TCCATATTGT CCCAGGCCAG CGCTTCTTTT GTGCTCCCAG ATTCCTGGGT GCAAGGTGGC     120

CTCATTAGTG CCCGGAGACC GCCCCATCTC CAGGGAGCAG ATAGACAGAC AAGGGGGTGA     180

TCAGGGGCAC AGTGATCCAA CCCTGGCCTC TGAACGCCGC AGCGGCCATT CCTTGGGCCC     240

AGCCTGGAGA CGGCCCCCCT GCAGCAGGCT AATCTTAGAC TTGCCTTTGT CTGGCCTGGG     300

TGTGGACGCA ATGTGCCTGT CAATTCCCCG CCACCTCAGA GCACTATAAA CCCCAGACCC     360

CTGGGAGTGG GTCACAATTG ACAGCCTCAA GGTTCCTGGC TTTTTGAACC ACCACAGACA     420

TCTCCTTTCC CGGCTACCCC ACCCTGAGCG CCAGACACCA TGAACCTTCC TTCCACAAAG     480

GTAAAGATCC AGGGATGGAG GGGTGACTCA GCCATCCCAG AGGAAGCAAA AAGAGTGCTT     540

GCTCAGAGGG CTGGAAGAAA GGCCAAAGGT GTCTCCACTC TTGGTCTTTT CCTGGGTGTG     600

CTCTGAGGCA GGAGCACCTG CCTTGGCTCA CATTGGGTTG GGTGCTGTTT TGCTAAGAGC     660

CTGTGTTTGC TGAGCTCATA TGTGTCAGGT GCTCCGTTTG CACCTGTCAT CTCTTGTCAT     720

CCTCCCAACA GCCTTGCAGA GTAGAAATTA TTTCTAGTAT ACCCAGTTTA CAGGTAAGGG     780
```

```
AGCTGTGCCC TCTGAAAGGG CAGGAAACTG GTTCAAAGCA ACGGAGTTCA GTCACTCCTG    840

CAAGGGGGCA GGCAGATGAG AGAGCATTCT GGAGTCTTGC TAGTTCCTGA TTTCCATGTG    900

TTTCCCTGCT GTGGAGAGGA AGTTGGGGGG ACTCAGTAGG GCCCGGGTTT TTCCCAAGTT    960

TACAACTTCT GCTGCAGACA GACACTCCTG TTTTCAGGTG GAGTGGCAAG TGCCCTAGTG   1020

GTGGCAACAG TGGCCTAAGT CTCCAGAGAA AAGGGGGATT CACTCTGCCC AGGGGGTCTC   1080

AAAAGGCTTC CTGTGGGAGA TGCTCTGCTG GGTCTTGAAG GAGGAGCAGG GAAAGTAGGC   1140

CGATACCAGC AAGGGCGCAA AGCAAGGAGA ACTAAGTGAC AGCCAGAAAG GAGTGCAGGC   1200

TTGGAGGGGG CGCGGAGCCA GAGGGCAGG TCCTGTGCGT GGGAGCTGGT GGCGGGCGCC    1260

GTGGAAGAC CCCCCCAGCG CCCTGTCTCC GTCTCCCTAG GTCTCCTGGG CCGCCGTGAC    1320

GCTACTGCTG CTGCTGCTGC TGCTGCCGCC CGCGCTGTTG TCGTCCGGGG CGGCTGCACA   1380

GCCCCTGCCC GACTGCTGTC GTCAAAAGAC TTGCTCTTGC CGCCTCTACG AGCTGCTGCA   1440

CGGCGCGGGC AATCACGCGG CCGGCATCCT CACGCTGGGC AAGCGGAGGT CCGGGCCCCC   1500

GGGCCTCCAG GGTCGGCTGC AGCGCCTCCT GCAGGCCAGC GGCAACCACG CCGCGGGCAT   1560

CCTGACCATG GGCCGCCGCG CAGGCGCAGA GCCAGCGCCG CGCCCCTGCC TCGGGCGCCG   1620

CTGTTCCGCC CCGGCCGCCG CCTCCGTCGC GCCCGGAGGA CAGTCCGGGA TCTGAGTCGT   1680

TCTTCGGGCC CTGTCCTGGC CCAGGCCTCT GCCCTCTGCC CACCCAGCGT CAGCCCCCAG   1740

AAAAAAGGCA ATAAAGACGA GTCTCCATTC GTGTGACTGG TCTCTGTTCC TGTGCGGTCG   1800

CGTCCTGCCC ATCCGGGGTG GCAAAGCGTC TTGCGGAGGA CAGCTGGGCC TGGAAGCCCG   1860

GCTGTCGGGC ACCAGCCTTA GCTTTTGCGT GGTTGAATCG GAAACACTCT TGGTTGGGGA   1920

GTTCCCAGTG CAAGGCCCTG GGCACAGAG AGAACTGCAC AGGTGCATGC                1970
```

(2) INFORMATION FOR SEQ ID NO: 2:

(i) SEQUENCE CHARACTERISTICS:
        (A) LENGTH: 131 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 2:

```
Met Asn Leu Pro Ser Thr Lys Val Ser Trp Ala Ala Val Thr Leu Leu
1               5                   10                  15

Leu Leu Leu Leu Leu Pro Pro Ala Leu Leu Ser Ser Gly Ala Ala
            20                  25                  30

Ala Gln Pro Leu Pro Asp Cys Cys Arg Gln Lys Thr Cys Ser Cys Arg
        35                  40                  45

Leu Tyr Glu Leu Leu His Gly Ala Gly Asn His Ala Ala Gly Ile Leu
    50                  55                  60

Thr Leu Gly Lys Arg Arg Ser Gly Pro Pro Gly Leu Gln Gly Arg Leu
65                  70                  75                  80

Gln Arg Leu Leu Gln Ala Ser Gly Asn His Ala Ala Gly Ile Leu Thr
                85                  90                  95

Met Gly Arg Arg Ala Gly Ala Glu Pro Ala Pro Arg Pro Cys Leu Gly
            100                 105                 110

Arg Arg Cys Ser Ala Pro Ala Ala Ala Ser Val Ala Pro Gly Gly Gln
        115                 120                 125

Ser Gly Ile
    130
```

(2) INFORMATION FOR SEQ ID NO: 3:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 3:

```
Gln Pro Leu Pro Asp Cys Cys Arg Gln Lys Thr Cys Ser Cys Arg Leu
1               5                   10                  15
Tyr Glu Leu Leu His Gly Ala Gly Asn His Ala Ala Gly Ile Leu Thr
            20                  25                  30
Leu
```

(2) INFORMATION FOR SEQ ID NO: 4:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 4:

```
Arg Ser Gly Pro Pro Gly Leu Gln Gly Arg Leu Gln Arg Leu Leu Gln
1               5                   10                  15
Ala Ser Gly Asn His Ala Ala Gly Ile Leu Thr Met
            20                  25
```

(2) INFORMATION FOR SEQ ID NO: 5:

(i) SEQUENCE CHARACTERISTICS:
        (A) LENGTH: 585 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

```
GGCTCGGCGG CCTCAGACTC CTTGGGTATT TGGACCACTG CACCGAAGAT ACCATCTCTC      60
CGGATTGCCT CTCCCTGAGC TCCAGACACC ATGAACCTTC CTTCTACAAA GGTTCCCTGG     120
GCCGCCGTGA CGCTGCTGCT GCTGCTACTG CTGCCGCCGG CGCTGCTGTC GCTTGGGGTG     180
GACGCGCAGC CTCTGCCCGA CTGCTGTCGC CAGAAGACGT GTTCCTGCCG TCTCTACGAA     240
CTGTTGCACG GAGCTGGCAA CCACGCCGCG GGCATCCTCA CTCTGGGAAA GCGGCGACCT     300
GGACCCCCAG GCCTCCAAGG ACGGCTGCAG CGCCTCCTTC AGGCCAACGG TAACCACGCA     360
GCTGGCATCC TGACCATGGG CCGCCGCGCA GGCGCAGAGC TAGAGCCATA TCCCTGCCCT     420
GGTCGCCGCT GTCCGACTGC AACCGCCACC GCTTTAGCGC CCCGGGGCGG ATCCAGAGTC     480
TGAACCCGTC TTCTATCCCT GTCCTAGTCC TAACTTTCCC CTCTCCTCGC CGGTCCCTAG     540
GCAATAAAGA CGTTTCTCTG CTAAAAAAAA AAAAAAAAAA AAAAA                     585
```

(2) INFORMATION FOR SEQ ID NO: 6:

(i) SEQUENCE CHARACTERISTICS:
        (A) LENGTH: 130 amino acids (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 6:

Met Asn Leu Pro Ser Thr Lys Val Pro Trp Ala Ala Val Thr Leu Leu
1               5                  10                  15

Leu Leu Leu Leu Leu Pro Pro Ala Leu Leu Ser Leu Gly Val Asp Ala
            20                  25                  30

Gln Pro Leu Pro Asp Cys Cys Arg Gln Lys Thr Cys Ser Cys Arg Leu
            35                  40                  45

Tyr Glu Leu Leu His Gly Ala Gly Asn His Ala Ala Gly Ile Leu Thr
        50                  55                  60

Leu Gly Lys Arg Arg Pro Gly Pro Gly Leu Gln Gly Arg Leu Gln
65                  70                  75                  80

Arg Leu Leu Gln Ala Asn Gly Asn His Ala Ala Gly Ile Leu Thr Met
                85                  90                  95

Gly Arg Arg Ala Gly Ala Glu Leu Glu Pro Tyr Pro Cys Pro Gly Arg
            100                 105                 110

Arg Cys Pro Thr Ala Thr Ala Thr Ala Leu Ala Pro Arg Gly Gly Ser
            115                 120                 125

Arg Val
130

(2) INFORMATION FOR SEQ ID NO: 7:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 7:

Met Asn Leu Pro Ser Thr Lys Val Pro Trp Ala Ala Val Thr Leu Leu
1               5                  10                  15

Leu Leu Leu Leu Leu Pro Pro Ala Leu Leu Ser Leu Gly Val Asp Ala
            20                  25                  30

(2) INFORMATION FOR SEQ ID NO: 8:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 8:

Gln Pro Leu Pro Asp Cys Cys Arg Gln Lys Thr Cys Ser Cys Arg Leu
1               5                  10                  15

Tyr Glu Leu Leu His Gly Ala Gly Asn His Ala Ala Gly Ile Leu Thr
            20                  25                  30

Leu (2) INFORMATION FOR SEQ ID NO: 9:

(i) SEQUENCE CHARACTERISTICS:

```
       (A) LENGTH: 27 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 9:

Pro Gly Pro Pro Gly Leu Gln Gly Arg Leu Gln Arg Leu Leu Gln Ala
1               5                   10                  15

Asn Gly Asn His Ala Ala Gly Ile Leu Thr Met
            20                  25

(2) INFORMATION FOR SEQ ID NO: 10:

(i) SEQUENCE CHARACTERISTICS:
       (A) LENGTH: 123 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 10:

Val Pro Trp Ala Ala Val Thr Leu Leu Leu Leu Leu Leu Pro Pro
1               5                   10                  15

Ala Leu Leu Ser Leu Gly Val Asp Ala Gln Pro Leu Pro Asp Cys Cys
            20                  25                  30

Arg Gln Lys Thr Cys Ser Cys Arg Leu Tyr Glu Leu Leu His Gly Ala
            35                  40                  45

Gly Asn His Ala Ala Gly Ile Leu Thr Leu Gly Lys Arg Arg Pro Gly
        50                  55                  60

Pro Pro Gly Leu Gln Gly Arg Leu Gln Arg Leu Leu Gln Ala Asn Gly
65                  70                  75                  80

Asn His Ala Ala Gly Ile Leu Thr Met Gly Arg Arg Ala Gly Ala Glu
                85                  90                  95

Leu Glu Pro His Pro Cys Ser Gly Arg Gly Cys Pro Thr Val Thr Thr
            100                 105                 110

Thr Ala Leu Ala Pro Arg Gly Gly Ser Gly Val
        115                 120

(2) INFORMATION FOR SEQ ID NO: 11:

(i) SEQUENCE CHARACTERISTICS:
       (A) LENGTH: 33 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 11:

Gln Pro Leu Pro Asp Cys Cys Arg Gln Lys Thr Cys Ser Cys Arg Leu
1               5                   10                  15

Tyr Glu Leu Leu His Gly Ala Gly Asn His Ala Ala Gly Ile Leu Thr
            20                  25                  30

Leu (2) INFORMATION FOR SEQ ID NO: 12:

(i) SEQUENCE CHARACTERISTICS:
       (A) LENGTH: 28 amino acids
       (B) TYPE: amino acid
```

(C) STRANDEDNESS: single
            (D) TOPOLOGY: linear (ii) MOLECULE TYPE: protein (xi) SEQUENCE DESCRIPTION: SEQ ID NO: 12:

Arg Pro Gly Pro Pro Gly Leu Gln Gly Arg Leu Gln Arg Leu Leu Gln
1               5                   10                  15

Ala Asn Gly Asn His Ala Ala Gly Ile Leu Thr Met
            20                  25

(2) INFORMATION FOR SEQ ID NO: 13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

CAACCNCTNC CNGACTGCTG                                           20

(2) INFORMATION FOR SEQ ID NO: 14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

ATNCCNGCNG CATGATT                                              17

(2) INFORMATION FOR SEQ ID NO: 15:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

GTTGCCAGCT CCGTGCAACA GTTCGTAGAG ACGG                           34

(2) INFORMATION FOR SEQ ID NO: 16:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 16:

CGGCAGGAAC ACGTCTTCTG GCG                                       23

(2) INFORMATION FOR SEQ ID NO: 17:

(i) SEQUENCE CHARACTERISTICS:
        (A) LENGTH: 30 base pairs
        (B) TYPE: nucleic acid (C) STRANDEDNESS: single
        (D) TOPOLOGY: linear (ii) MOLECULE TYPE: cDNA (xi) SEQUENCE DESCRIPTION: SEQ ID NO: 17:

TCCTTGGGTA TTTGGACCAC TGCACCGAAG                                30

(2) INFORMATION FOR SEQ ID NO: 18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 18:

ATACCATCTC TCCGGATTGC CTCTCCCTGA                                30

(2) INFORMATION FOR SEQ ID NO: 19:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 19:

CCTCTGAAGG TTCCAGAATC GATAGTAN                                  28

(2) INFORMATION FOR SEQ ID NO: 20:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 20:

CCTCTGAAGG TTCCAGAATC GATAG                                     25

(2) INFORMATION FOR SEQ ID NO: 21:

(i) SEQUENCE CHARACTERISTICS:
        (A) LENGTH: 577 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 21:

CACAATTGAC AGCCTCAAGG TTCCTGGCTT TTTGAACCAC CACAGACATC TCCTTTCCCG    60

GCTACCCCAC CCTGAGCGCC AGACACCATG AACCTTCCTT CCACAAAGGT CTCCTGGGCC   120

GCCGTGACGC TACTGCTGCT GCTGCTGCTG CTGCCGCCCG CGCTGTTGTC GTCCGGGGCG   180

GCTGCACAGC CCCTGCCCGA CTGCTGTCGT CAAAAGACTT GCTCTTGCCG CCTCTACGAG   240

CTGCTGCACG GCGCGGGCAA TCACGCGGCC GGCATCCTCA CGCTGGGCAA GCGGAGGTCC   300

GGGCCCCCGG GCCTCCAGGG TCGGCTGCAG CGCCTCCTGC AGGCCAGCGG CAACCACGCC   360

| | |
|---|---|
| GCGGGCATCC TGACCATGGG CCGCCGCGCA GGCGCAGAGC CAGCGCCGCG CCCCTGCCTC | 420 |
| GGGCGCCGCT GTTCCGCCCC GGCCGCCGCC TCCGTCGCGC CCGGAGGACA GTCCGGGATC | 480 |
| TGAGTCGTTC TTCGGGCCCT GTCCTGGCCC AGGCCTCTGC CCTCTGCCCA CCCAGCGTCA | 540 |
| GCCCCCAGAA AAAAGGCAAT AAAGACGAGT CTCCATT | 577 |